(12) United States Patent
Hong et al.

(10) Patent No.: US 9,579,607 B2
(45) Date of Patent: Feb. 28, 2017

(54) DEVICE FOR MEASURING POLLUTION INDEX OF FILTRATION MEMBRANE

(71) Applicant: DOOSAN HEAVY INDUSTRIES & CONSTRUCTION CO., LTD., Changwon-si, Gyeongsangnam-do (KR)

(72) Inventors: Seung-Kwan Hong, Yongin-si (KR); Il-Gu Hong, Namyangju-si (KR); Young Gil Ju, Daejeon (KR)

(73) Assignee: DOOSAN HEAVY INDUSTRIES & CONSTRUCTION CO., LTD., Changwon-si (KR)

( * ) Notice: Subject to any disclaimer, the term of this patent is extended or adjusted under 35 U.S.C. 154(b) by 281 days.

(21) Appl. No.: 14/371,122

(22) PCT Filed: Nov. 20, 2012

(86) PCT No.: PCT/KR2012/009837
§ 371 (c)(1),
(2) Date: Jul. 8, 2014

(87) PCT Pub. No.: WO2013/105728
PCT Pub. Date: Jul. 18, 2013

(65) Prior Publication Data
US 2015/0013434 A1 Jan. 15, 2015

(30) Foreign Application Priority Data

Jan. 9, 2012 (KR) .................... 10-2012-0002412

(51) Int. Cl.
*G01N 15/08* (2006.01)
*B01D 65/10* (2006.01)
(Continued)

(52) U.S. Cl.
CPC ............. *B01D 65/10* (2013.01); *B01D 61/22* (2013.01); *C02F 1/441* (2013.01); *C02F 1/442* (2013.01);
(Continued)

(58) Field of Classification Search
CPC .... B01D 2311/16; B01D 61/22; B01D 65/10; C02F 1/441; C02F 1/442; C02F 2209/00;
(Continued)

(56) References Cited

U.S. PATENT DOCUMENTS

2012/0222999 A1* 9/2012 Ha ........................ C02F 1/008
210/175
2013/0055794 A1* 3/2013 Armour ............... H04N 7/0115
73/38
(Continued)

FOREIGN PATENT DOCUMENTS

JP 6-21728 U 3/1994
JP 10-156156 A 6/1998
(Continued)

OTHER PUBLICATIONS

International Search Report for PCT/KR2012/009837 dated Feb. 28, 2013.

*Primary Examiner* — Francis Gray
(74) *Attorney, Agent, or Firm* — Sughrue Mion, PLLC (57) ABSTRACT

A device for measuring the pollution index of a filtration membrane includes: a raw water supply part; a first filtration membrane; a raw water supply line; a first flow rate measuring part; a first path line; a second path line; a second filtration membrane having a filtration characteristic different from the first filtration membrane; a first path selection valve installed in the first path line in parallel with respect to the second filtration membrane so that a first measuring path from the raw water supply part to the first flow rate (Continued)

measuring part passes through the first filtration membrane and a second measuring path from the raw water supply part to the first flow rate measuring part successively passes through the first and second filtration membranes; and a pollution index measuring part measuring the pollution indexes of the first and second filtration membranes.

17 Claims, 5 Drawing Sheets (51) Int. Cl.
*B01D 61/22* (2006.01)
*C02F 1/44* (2006.01)
*C02F 103/08* (2006.01)

(52) U.S. Cl.
CPC ...... *G01N 15/0826* (2013.01); *B01D 2311/16* (2013.01); *C02F 2103/08* (2013.01); *C02F 2209/00* (2013.01); *G01N 2015/084* (2013.01); *G01N 2015/086* (2013.01)

(58) Field of Classification Search
CPC ......... G01N 15/0826; G01N 2015/084; G01N 2015/086
See application file for complete search history.

(56) References Cited

U.S. PATENT DOCUMENTS

| 2013/0277222 A1* | 10/2013 | Kwon | C02F 1/4691 204/555 |
| 2014/0080115 A1* | 3/2014 | Reed | G01N 15/0618 435/3 |
| 2016/0016833 A1* | 1/2016 | Okajima | B01D 65/02 210/620 |

FOREIGN PATENT DOCUMENTS

| JP | 10-180047 A | 7/1998 |
| JP | 2009-72756 A | 4/2009 |
| KR | 10-2010-0057262 A | 5/2010 |
| KR | 10-2011-0089710 A | 8/2011 |

* cited by examiner

DEVICE FOR MEASURING POLLUTION INDEX OF FILTRATION MEMBRANE

CROSS REFERENCE TO RELATED APPLICATIONS

This application is a National Stage of International Application No. PCT/KR2012/009837, filed on Nov. 20, 2012, which claims priority from Korean Patent Application No. 10-2012/0002412, filed on Jan. 9, 2012, the contents of all of which are incorporated herein by reference in their entirety.

TECHNICAL FIELD

The present invention relates to a device for measuring the pollution index of a filtration membrane, and more particularly, to a device for measuring the pollution index of a filtration membrane which measures the degree of filtration membrane fouling more precisely caused by particulate materials, colloids, organic matters, etc in a seawater desalination process using reverse osmosis or a nanofiltration process.

BACKGROUND ART

Reverse osmosis and nanofiltration are one of the technologies that have recently gained attention in the water treatment field. Especially, processes using reverse osmosis are now coming into widespread use in the field of seawater desalination or sewage recycling.

According to a Global Water Intelligence special report entitled "Water Reuse Markets 2005-2015: A Global Assessment & Forecast", global water reuse capacity is expected to grow from 2 million tons a day today to 5.4 million tons per day in 2015. Over the same period, global desalination capacity is expected to grow from 3 million tons per day to 6.2 million tons per day. Besides, reverse osmosis and nanofiltration are advanced water treatment technologies which are getting attention in the field of surface water and ground water treatment, industrial wastewater treatment, and zero-discharge recycling.

However, membrane fouling, i.e., filtration membrane fouling, has an obstacles to the commercialization or the on-site installation and operation of these membranes of reverse osmosis and nanofiltration. Membrane fouling refers to a situation in which foreign substances present in water flowing into a filtration membrane are deposited or adsorbed on the surface of the filtration membrane in a way that degrades the water permeability of the filtration membrane.

There are various types of foreign substances causing membrane fouling, including suspended particles, colloids, organic matters, microbes, and mineral salts such as calcium salts. It is considerably difficult to predict membrane fouling because of these various foreign substances causing membrane fouling.

In general, the SDI (Silt Density Index) is used to predict membrane fouling occurring in reverse osmosis or nanofiltration. The SDI is a measure of the rate at which membrane fouling will occur. The SDI is a method of measurement where influent water is passed through a 0.45 µm pore size filter with 47 mm diameter at a pressure of 30 psi to measure the degree of fouling of membranes by suspended solids (SS).

The initial time $T_0$ to filter 500 ml of water is measured, and then the time $T_1$ to filter 500 ml of water is measured again after 15 minutes. The ratio of $T_0$ to $T_1$ is used as a measure of membrane fouling.

The SDI measuring method is currently the most widely used method to predict the propensity for membrane fouling by influent water in reverse osmosis or nanofiltration. Typically, an SDI value less than 3 is considered to be acceptable, and an SDI value greater than 5 indicates that severe fouling will occur.

However, the above-described SDI has its limits in that it does not use the same situation occurring in a reverse osmosis membrane (RO membrane). That is, the SDI is an indirect method of evaluating the fouling potential of suspended particles larger than 0.45 µm on membranes. Therefore, the SDI cannot evaluate the effects of fine materials such as colloids or organic matters smaller than 0.45 µm.

Moreover, reverse osmosis and nanofiltration systems are operated in a cross-flow mode in which influent water flows in a direction orthogonal to the permeation direction of a filtration membrane, thus making it impossible to measure the surface characteristics of foulants, the main cause of membrane fouling, by the SDI. Accordingly, much research revealed that SDI measurements are different from actual results of operations.

Although MFI (Modified Fouling Index) can be used to compensate for these problems of the SDI, a limited range of membrane foulants are available for this method because the MFI and the SDI basically use the same filtration membrane.

To overcome this, methods such as MFI-UF (Modified fouling index—Ultrafilter) or MFI-NF (Modified fouling index—Nanofilter) were proposed. However, these methods cannot predict the propensity for various types of membrane fouling that may occur in a filtration membrane because they also use a single type of membrane.

In view of this, the present inventor suggested earlier-filed Korean Patent Registration No. 106901 titled 'Device for measuring pollution index of membrane'. The device for measuring the pollution index of a membrane disclosed in the-above Korean Patent Registration is a device for measuring the pollution index of a membrane that predicts membrane fouling, in advance, caused by hydrophilic and hydrophobic particulate materials, colloids, organic matters, etc in a water treatment process using a reverse osmosis membrane or nanofiltration membrane. This device is characterized in that different types of filtration membranes such as hydrophilic microfiltration membranes, hydrophobic microfiltration membranes, and ultrafiltration membranes are combined together to quantify the intensity of membrane fouling by various types of membrane foulants present in influent water to be treated by reverse osmosis or nanofiltration.

The above-mentioned Korean Patent Registration is advantageous in that the measurement can be done simply due to parallel connection and the evaluation differs depending on the properties of membrane foulants, but disadvantageous in that it is difficult to separate different types of membrane fouling according to membrane foulants source and evaluate them.

In addition, the present inventor proposed earlier-filed Korean Unexamined Patent Application No. 2011-0089719 titled 'Device for predicting pollution index of membrane'. In this Korean Unexamined Patent Application, different types of membranes foulants can be separated and evaluated by connecting a plurality of filtration membranes with different filtration characteristics in series. However, this patent application is disadvantageous in that three filtration membranes, three pumps, and three tanks are required and a relatively long period of time is needed for the measurement because of the serial structure.

DISCLOSURE OF THE INVENTION

The present invention has been made in an effort to solve the above problems occurring in the related art, and to provide a device for measuring the pollution index of a filtration membrane which predicts filtration membrane fouling more precisely caused by particulate materials, colloids, organic matters, etc in a seawater desalination process using reverse osmosis or a nanofiltration process, and quantifies the degree of membrane fouling by different types of membrane foulants present in seawater by combining together different types of filtration membranes such as hydrophilic microfiltration membranes, hydrophobic microfiltration membranes, and ultrafiltration membranes.

Furthermore, the present invention provides a device for measuring the pollution index of a filtration membrane which is suitable for use with seawater desalination plants or portable measuring equipment due to its simple structure, ensures the accuracy of measurement, and cuts down measurement time.

To achieve the above objects, one embodiment of the present invention provides a device for measuring the pollution index of a filtration membrane which includes: a raw water supply part supplying raw water to be measured; a first filtration membrane; a raw water supply line connecting the raw water supply part to the first filtration membrane; a first flow rate measuring part measuring the flow rate; a first path line connecting the first filtration membrane to the first flow rate measuring part; a second path line connected to the first path line in parallel; a second filtration membrane installed in the second path line and having a filtration characteristic different from the first filtration membrane; a first path selection valve installed in the first path line in parallel with respect to the second filtration membrane so that a first measuring path through which the raw water flows from the raw water supply part to the first flow rate measuring part passes through the first filtration membrane and a second measuring path through which the raw water flows from the raw water supply part to the first flow rate measuring part successively passes through the first filtration membrane and the second filtration membrane; and a pollution index measuring part measuring the pollution indexes of the first filtration membrane and the second filtration membrane on the basis of the flow rate measured by the first flow rate measuring part with respect to the first measuring path and the second measuring path.

The pores of the first filtration membrane may be larger than the pores of the second filtration membrane.

The device may further include: a first pressure regulator installed on the inlet side of the first filtration membrane of the raw water supply line to regulate the pressure of raw water introduced into the first filtration membrane; a first bypass line connected to the raw water supply line to bypass the first pressure regulator; and a first bypass valve installed on the first bypass line, and closed to form the first measuring path and opened to form the second measuring path and the third measuring path.

The device may further include: a second pressure regulator installed on the inlet side of the second filtration membrane of the second path line to regulate the pressure of raw water introduced into the second filtration membrane.

The second path line may include a second inlet path line forming the inlet side of the second filtration membrane and a second outlet path line forming the outlet side of the second filtration membrane, the device may further include a third path line connected in parallel to the second outlet path line, a third filtration membrane installed on the third path line and having pores smaller than the pores of the second filtration membrane, and a second path selection valve installed on the second path line in parallel to the third filtration membrane to form a third measuring path, while the first path selection valve is in closed position, along which the raw water from the raw water supply part sequentially passes through the first, second, and third filtration membranes and flows to the first flow measuring part, and the pollution index measuring part may measure the pollution index of the third filtration membrane on the basis of the flow rate measured by the first flow rate measuring part with respect to the third measuring path.

The device may further include: a second pressure regulator installed on the second inlet path line to regulate the pressure of raw water introduced into the second filtration membrane; a second bypass line connected to the second inlet path line to bypass the second pressure regulator; and a second bypass valve installed on the second bypass line, and closed to form the first measuring path and the second measuring path and opened to form the third measuring path.

The device may further include: a third pressure regulator installed on the inlet side of the third filtration membrane of the third path line to regulate the pressure of raw water introduced into the third filtration membrane.

The device may further include: a first path control valve installed on the inlet side of the first pressure regulator of the raw water supply line so as to be connected in parallel to the first bypass valve, and opened or closed in reverse to the way the first bypass valve is opened or closed; a second path control valve installed on the inlet side of the second pressure regulator of the second path line so as to be connected in parallel to the second bypass valve, and closed to form the first measuring path and the third measuring path and opened to form the second measuring path; and a third path control valve installed on the inlet side of the third pressure regulator of the third path line and opened to form the third measuring path.

The pollution index measuring part may measure the pollution indexes of the first, second, and third filtration membranes with respect to the first, second, and third filtration membranes, respectively, in descending order.

The pollution index measuring part may measure the pollution indexes of the first, second, and third filtration membranes with respect to the first, second, and third filtration membranes, respectively, in ascending order.

The device may further include: a third path line branched from the inlet side of the second filtration membrane of the second path line; a third filtration membrane installed on the third path line and having pores smaller than the pores of the second filtration membrane; an auxiliary filtration membrane installed on the inlet side of the third filtration membrane of the third path line and having pores equal in size to the pores of the second filtration membrane; and a second flow rate measuring part installed on the outlet side of the third filtration membrane of the third path line to form a third measuring path along which the raw water from the raw water supply part sequentially passes through the first, auxiliary, and third filtration membranes and flows to the second flow measuring part, the second measuring path and the third measuring path may be formed simultaneously, and the pollution index measuring part may measure the pollution index of the third filtration membrane on the basis of the flow rate measured by the second flow rate measuring part with respect to the third measuring path.

The device may further include: a first pressure regulator installed on the raw water supply line to regulate the pressure of raw water introduced into the first filtration membrane; a second pressure regulator installed on the inlet side of the second filtration membrane of the second path line to regulate the pressure of raw water introduced into the second filtration membrane; and a third pressure regulator installed between the auxiliary filtration membrane of the third path line and the third filtration membrane to regulate the pressure of raw water introduced into the third filtration membrane.

The device may further include: a first bypass line connected to the raw water supply line to bypass the first pressure regulator; and a first bypass valve installed on the first bypass line, and closed to form the first measuring path and opened to form the second measuring path and the third measuring path.

The device may further include: a first path control valve installed on the inlet side of the first pressure regulator of the raw water supply line so as to be connected in parallel to the first bypass valve, and opened or closed in reverse to the way the first bypass valve is opened or closed; and a fourth path control valve installed on the second path line to control the inflow of raw water to the second path line, and closed to form the first measuring path and opened to form the second measuring path.

To achieve the above objects, another embodiment of the present invention provides a device for measuring the pollution index of a filtration membrane which includes: a raw water supply part supplying raw water to be measured; a plurality of filtration membranes having different filtration properties; a path line connecting the plurality of filtration membranes in parallel to the raw water supply part; a plurality of flow measuring parts installed on the outlet sides of the filtration membranes to correspond to the respective filtration membranes, and measuring the flow rate of raw water passed through the filtration membranes; at least one auxiliary filtration membrane installed on the inlet side of at least one of the plurality of filtration membranes, and having a different filtration characteristic from that of the at least one filtration membrane; and a pollution index measuring part measuring the pollution indexes of the filtration membranes on the basis of the flow rates measured by the flow rate measuring parts.

The plurality of filtration membranes may have different pore sizes, and the pores of the auxiliary filtration membrane may be larger than the pores of the filtration membranes.

The device may further include pressure regulators respectively installed on the inlet sides of the filtration membranes to regulate the pressure of raw water introduced into the filtration membranes.

Advantageous Effects

According to the above configuration, the present invention provides a device for measuring the pollution index of a filtration membrane which is suitable for use with seawater desalination plants or portable measuring equipment due to its simple structure, ensures the accuracy of measurement, and cuts down measurement time.

BRIEF DESCRIPTION OF THE DRAWINGS

These and other objects, features, aspects, and advantages of preferred embodiments of the present invention will be more fully described in the following detailed description, taken in conjunction with the accompanying drawings. In the drawings.

[Explanation of Reference Numerals]

| | |
|---|---|
| 10: Raw water supply line | 21: First path line |
| 22: Second path line | 23: Third path line |
| 41: First path selection valve | 42: Second path selection valve |
| 51: First bypass valve | 42: Second path selection valve |
| 61: First pressure regulator | 62: Second pressure regulator |
| 63: Third pressure regulator | 71: First bypass line |
| 72: Second bypass line | 81: First path control valve |
| 82: Second path control valve | 83: First path control valve |
| 110: First filtration membrane | 120: second filtration valve |
| 130: Third filtration membrane | 200: Raw water supply part |
| 310: First flow rate measuring part | 320: Second flow rate measuring part |
| 400: Pollution index measuring part | |

MODES FOR CARRYING OUT THE PREFERRED EMBODIMENTS

A device for measuring the pollution index of a filtration membrane according to the present invention includes: a raw water supply part supplying raw water to be measured; a first filtration membrane; a raw water supply line connecting the raw water supply part to the first filtration membrane; a first flow rate measuring part measuring the flow rate; a first path line connecting the first filtration membrane to the first flow rate measuring part; a second path line connected to the first path line in parallel; a second filtration membrane installed in the second path line and having a filtration characteristic different from the first filtration membrane; a first path selection valve installed in the first path line in parallel with respect to the second filtration membrane so that a first measuring path through which the raw water flows from the raw water supply part to the first flow rate measuring part passes through the first filtration membrane and a second measuring path through which the raw water flows from the raw water supply part to the first flow rate measuring part successively passes through the first filtration membrane and the second filtration membrane; and a pollution index measuring part measuring the pollution indexes of the first filtration membrane and the second filtration membrane on the basis of the flow rate measured by the first flow rate measuring part with respect to the first measuring path and the second measuring path.

BEST MODE FOR CARRYING OUT THE INVENTION

Hereinafter, embodiments of the present invention will be described in detail with reference to the accompanying drawings. In describing the embodiments of the present invention, the same reference numerals are used throughout the drawings to refer to the same elements, and redundant descriptions thereof are omitted if necessary.

First Embodiment

Figure 1:
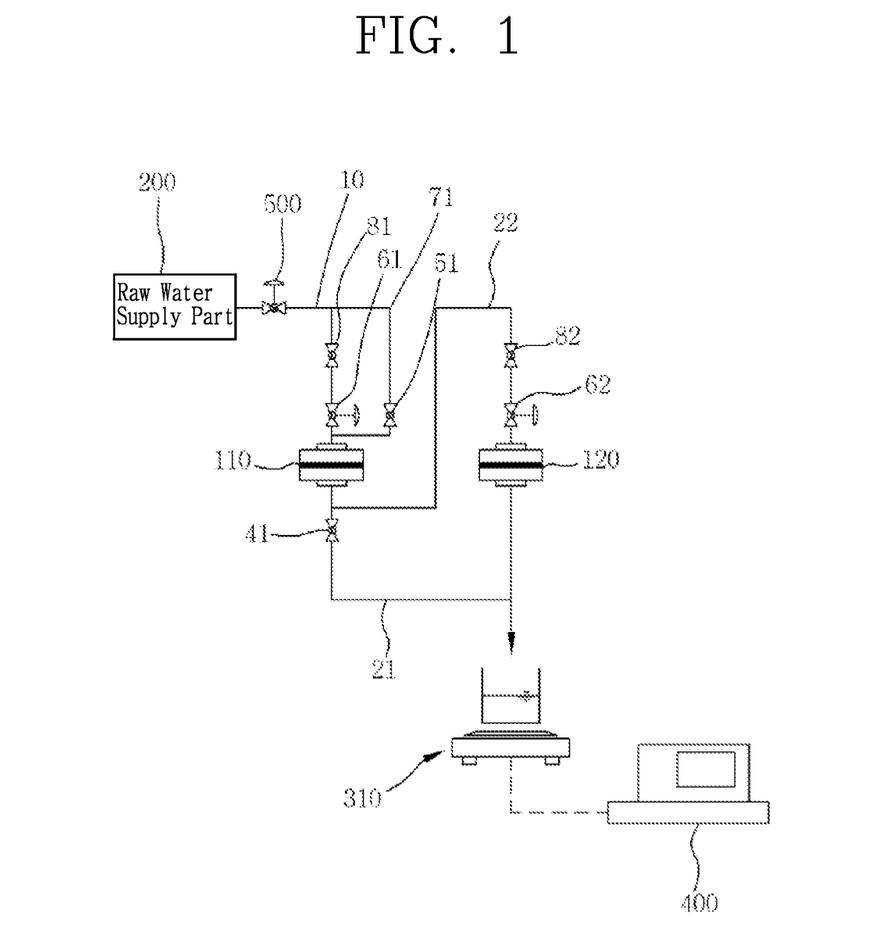
FIG. 1 is a view showing the configuration of a device for measuring the pollution index of a filtration membrane according to a first embodiment of the present invention.

FIG. 1 is a view showing the configuration of a device for measuring the pollution index of a filtration membrane according to a first embodiment of the present invention. Referring to FIG. 1, the device for measuring the pollution index of a filtration membrane according to the first embodiment of the present invention includes a raw water supply part 200, a first filtration membrane 110, a second filtration membrane 120, a first flow rate measuring part 310, a first path line 21, a second path line 22, a first path selection valve 41, and a pollution index measuring part 400.

The raw water supply part 200 supplies raw water to be measured. The raw water supply part 200 is configured to supply raw water in a pressurized condition using compressed air, a pump, etc. For a seawater desalination plant, raw water may be supplied in a compressed state by a high-pressure pump of the plant.

The first filtration membrane 110 and the second filtration membrane 120 have different filtration properties. In an example of the present invention, the first filtration membrane 110 and the second filtration membrane 120 have different pore sizes. For example, the pores of the first filtration membrane 110 are larger than the pores of the second filtration membrane 120.

For example, if a hydrophilic microfiltration membrane MF is used as the first filtration membrane 110, a hydrophilic ultrafine UF or hydrophilic nanofiltration membrane NF having smaller pores than the hydrophilic microfiltration membrane MF may be used as the second filtration membrane 120. Also, if the hydrophilic ultrafiltration membrane UF is used as the first filtration membrane 110, the hydrophilic nanofiltration membrane NF may be used as the second filtration membrane 120.

A raw water supply line 10 connects the raw water supply part 200 to the first filtration membrane 110 so that the raw water from the raw water supply part 200 flows into the first filtration membrane 110 through the raw water supply line 10. A supply side pressure regulator 500 may be installed on the raw water supply line 10 to regulate the pressure of raw water supplied from the raw water supply part 200.

The first flow rate measuring part 310 measures flow rate. That is, it measures the flow rate of raw water filtered through the first filtration membrane 110 via a first measuring path to be described later and the flow rate of raw water filtered through the second filtration membrane 120 via a second measuring path to be described later. A detailed description of this will be described later.

The first path line 21 connects the first filtration membrane 110 to the first flow rate measuring part 310 so that the raw water filtered through the first filtration membrane 110 flows to the first flow rate measuring part 310. The second path line 22 is connected in parallel to the first path line 21, as shown in FIG. 1.

The first path selection valve 41 is installed on the first path line 31 so as to be connected in parallel to the second filtration membrane 120. The first path selection valve 41 is opened to form a first measuring path or closed to form a second measuring path. More specifically, when the first path selection valve 41 is opened, the first measuring path is formed along which the raw water from the raw water supply part 200 passes through the raw water supply line 10, the first filtration membrane 110, and the first path line 21 and flows to the first flow rate measuring part 310.

On the other hand, when the first path selection valve 41 is closed, raw water from the raw water supply part 200 passes through the raw water supply line 10, the first filtration membrane 110, and the second path line 22, is filtered through the second filtration membrane 120, and flows to the first flow rate measuring part 310.

According to the above configuration, the pollution index measuring part 400 measures the pollution indexes of the first filtration membrane 110 and second filtration membrane 120 on the basis of the flow rates measured for the first and second measuring paths by the first flow rate measuring part 310.

More specifically, when the first path selection valve 41 is opened, the pollution index measuring part 400 measures the pollution index of the first filtration membrane 110 by measuring the flow rate of water filtered through the first filtration membrane 110 alone via the first measuring path. Then, when the first path selection valve 41 is closed, the pollution index measuring part 400 measures the pollution index of the second filtration membrane 120 by measuring the flow rate of water sequentially filtered through the first filtration membrane 110 and the second filtration membrane 120 along the second measuring path.

Accordingly, the pollution indexes of the first and second filtration membranes 110 and 120 having different filtration properties are measured individually. The raw water passed through the first filtration membrane 110 is filtered through the second filtration membrane 120 having smaller pores than the first filtration membrane 110. This causes foreign substances having large particle size to be firstly filtered through the first filtration membrane 110, thus allowing for more precise measurement of the effects of particles on fouling of the second filtration membrane 120.

For example, if the hydrophilic microfiltration membrane MF is used as the first filtration membrane 110, common suspended particles are deposited or adsorbed on the surface of the first filtration membrane 110. On the other hand, if the hydrophilic ultrafiltration membrane UF is used as the second filtration membrane 120, colloid particles are deposited or adsorbed on the surface of the second filtration membrane 120. Accordingly, it is possible to differentiate between membrane fouling caused by the deposition or adsorption of common suspended particles membrane fouling caused by colloids and evaluate the different types of membrane fouling by filtering raw water through the second filtration membrane 120 alone and measuring the degree of fouling of the second filtration membrane 120.

Also, the first filtration membrane 110 and the second filtration membrane 120 are measured separately by means of the first path valve 41, and one raw supply part 200 and one first flow rate measuring part 310 enable accurate measurement of the degree of fouling of the first and second filtration membranes 110 and 120.

As shown in FIG. 1, the device for measuring the pollution index of a filtration membrane according to the first embodiment of the present invention may include a first pressure regulator 61, a first bypass line 71, and a first bypass valve 51.

The first pressure regulator 61 is installed on the inlet side of the first filtration membrane 110 of the raw water supply line 10 to regulate the pressure of raw water introduced into the first filtration membrane 110. The first bypass line 71 is connected in parallel to the raw water supply line 10 to bypass the first pressure regulator 61.

The first bypass valve 51 is installed on the first bypass line 71. When the first measuring path is formed, i.e., the first path selection valve 41 is opened, the first bypass valve 51 is closed to let the raw water supplied through the raw water supply line 10 into the first filtration membrane 110 through the first pressure regulator 61.

On the other hand, when the second measuring path is formed, i.e., the first path selection valve 41 is closed, the first bypass valve 51 is opened to let the raw water supplied through the raw water supply line 10 into the first filtration membrane 110 through the first bypass line 71.

As shown in FIG. 1, the device for measuring the pollution index of a filtration membrane according to the first embodiment of the present invention may include a second pressure regulator 62 that is installed on the inlet side of the second filtration membrane 120 of the second path line 22 and regulates the pressure of raw water introduced into the second filtration membrane 120.

As described above, the first pressure regulator 61 and the second pressure regulator 62 are respectively installed on the inlet sides of the first and second filtration membranes 110 and 120, and the hydraulic pressure of raw water passing through the first and second filtration membranes 110 and 120 is kept constant, thereby enabling more accurate measurement.

Also, when forming the second measuring path for measuring the degree of fouling of the second filtration membrane 120, raw water is not passed through the first pressure regulator 61, but instead bypassed through the first bypass line 71 to pass through the first filtration membrane 110. Thus, the pressure for measuring the degree of fouling of the second filtration membrane 120 by means of the first pressure regulator 61 can be set higher than the pressure for measuring the degree of fouling of the first filtration membrane 110.

As shown in FIG. 1, the device for measuring the pollution index of a filtration membrane according to the first embodiment of the present invention may include a first path control valve 82 and a second path control valve 82. The first path control valve 81 is installed on the inlet side of the first pressure regulator 61 of the raw water supply line 10 so as to be connected in parallel to the first bypass valve 51. The second path control valve 82 is installed on the inlet side of the second pressure regulator 62 of the second path line 22.

The first path control valve 81 is opened or closed in reverse to the way the first bypass valve 51 is opened or closed. That is, when forming the first measuring path, the first bypass valve 51 is closed and the first path control valve 81 is opened and raw water flows into the first filtration membrane 110 through the first pressure regulator 61. On the other hand, when forming the second measuring path, the first bypass valve 51 is opened and the first bypass control valve 81 is closed and raw water flows into the first filtration membrane 110 through the first bypass line 71. The second path control valve 81 is closed when forming the first measuring path, and it is opened when forming the second measuring path.

Accordingly, once the first measuring path is formed, raw water is completely prevented from flowing to the second pressure regulator 62, and once the second measuring path is formed, raw water is likewise prevented from flowing to the first pressure regulator 61. Therefore, the first and second measuring paths can be formed in a more stable manner than preventing the flow of raw water only by means of the first and second pressure regulators 61 and 62.

Second Embodiment

Hereinafter, the configuration of a device for measuring the pollution index of a filtration membrane according to a second embodiment of the present invention will be described in detail with reference to FIG. 2. The device for measuring the pollution index of a filtration membrane according to the second embodiment of the present invention uses three filtration membranes having different pore characteristics, and includes more components in addition to those in the first embodiment. The components corresponding to those of the first embodiment are denoted by the same reference numerals, and a description thereof can be omitted.

The second embodiment of the present invention will be described on an example where the hydrophilic microfiltration membrane MF is used as the first filtration membrane 110, the hydrophilic ultrafiltration membrane is used as the second filtration membrane 120, and the hydrophilic nanofiltration membrane NF is used as a third filtration membrane 130.

Figure 2:
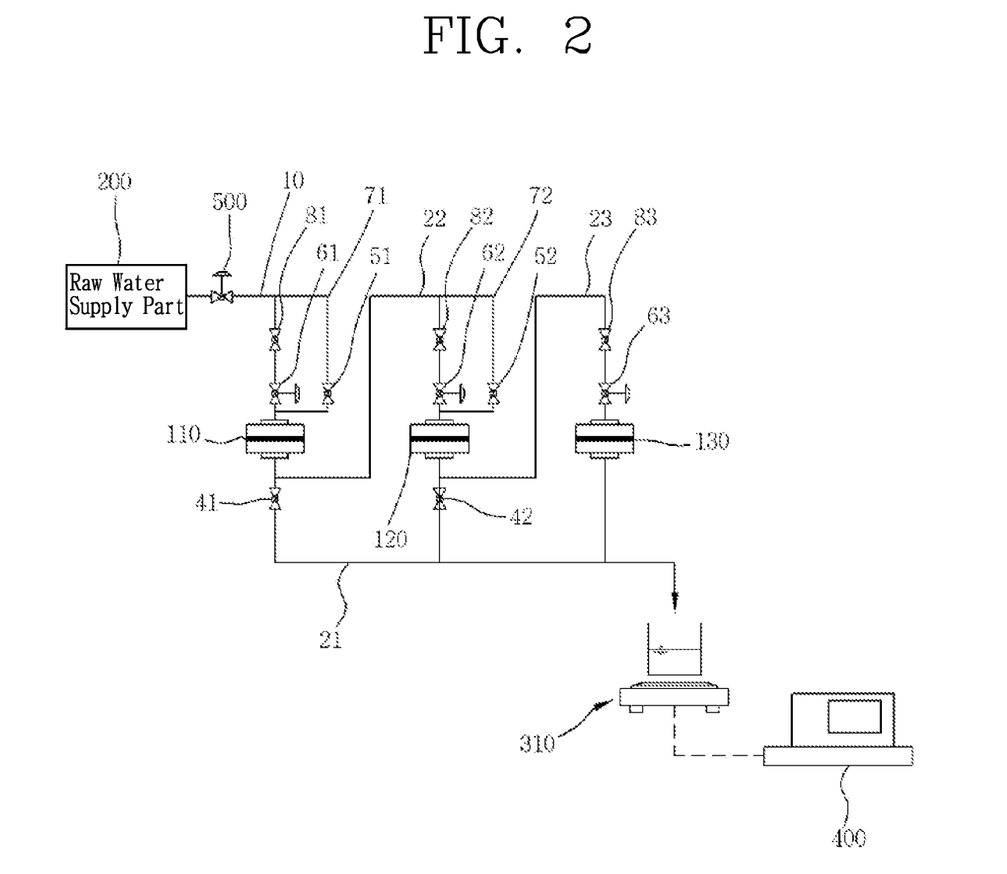
FIG. 2 is a view showing the configuration of a device for measuring the pollution index of a filtration membrane according to a second embodiment of the present invention.

Referring to FIG. 2, the device for measuring the pollution index of a filtration membrane according to the second embodiment of the present invention includes a raw water supply part 200, a raw water supply line 10, a first filtration membrane 110, a second filtration membrane 120, a third filtration membrane 130, a first flow rate measuring part 310, a first path line 21, a second path line 22, a third path line 23, a first path selection valve 41, a second path selection valve 42, a first flow rate measuring part 310, and a pollution index measuring part 400. The basic configurations of the raw water supply part 200 and the first flow rate measuring part 310 are identical to those of the first embodiment, so a detailed description thereof will be omitted.

The first path line 21 connects the first filtration membrane 110 to the first flow rate measuring part 310 so that the raw water filtered through the first filtration membrane 110 flows to the first flow rate measuring part 310. The second path line 22 is connected in parallel to the first path line 21, like the first embodiment.

The first path selection valve 41 is installed on the first path line 31 so as to be connected in parallel to the second filtration membrane 120. The first path selection valve 41 is opened to form a first measuring path or closed to form second and third measuring paths, and a detailed description of which will be made later.

The second path line 22 may be divided into a second inlet path line forming the inlet side of the second filtration membrane 120 and a second outlet path line forming the outlet side of the second filtration membrane 120 with respect to the second filtration membrane 120. As shown in FIG. 2, the third path line 23 is connected in parallel to the second outlet path line.

The third filtration membrane 130 is installed on the third path line 23. As described above, the hydrophilic nanofiltration membrane NF having smaller pores than the first and second filtration membranes 110 and 120 is used as the third filtration membrane 130.

The second path selection valve 42 is installed on the second path line 22 in parallel to the third filtration membrane 130. When the first path selection valve 41 is closed, the second path selection valve 42 is closed to allow raw water from the raw water supply part 200 to sequentially pass through the first filtration membrane 110, the second filtration membrane 120, and the third filtration membrane 130 and flows to the first flow rate measuring part 310.

The device for measuring the pollution index of a filtration membrane according to the second embodiment of the present invention may include a first pressure regulator 61, a first bypass line 71, and a first bypass valve 51. Moreover, the device for measuring the pollution index of a filtration membrane according to the second embodiment of the present invention may include a second pressure regulator 62, a second bypass line 72, a second bypass valve 52, and a third pressure regulator 63.

The first pressure regulator 61 is installed on the inlet side of the first filtration membrane 110 of the raw water supply line 10 to regulate the pressure of raw water introduced into the first filtration membrane 110. The first bypass line 71 is connected in parallel to the raw water supply line 10 to bypass the first pressure regulator 61. The first bypass valve 51 is installed on the first bypass line 71.

The second pressure regulator 62 is likewise installed on the second inlet path line of the second path line 22 to regulate the pressure of raw water introduced into the second filtration membrane 120. The second bypass line 72 is connected to the second inlet path line to bypass the second pressure regulator 62, and the second bypass valve 52 is installed on the second bypass line 72. The third pressure regulator 63 is installed on the inlet side of the third filtration membrane 130 of the third path line 23 to regulate the pressure of raw water introduced into the third filtration membrane 130.

According to the above configuration, a process for measuring the pollution indexes of the first, second, and third filtration membranes 110, 120, and 130 on the basis of the flow rates measured by the first flow rate measuring part 310 will be described in detail.

For example, the device for measuring the pollution index of a filtration membrane measures the pollution indexes of the first, second, and third filtration membranes 110, 120, and 130 in ascending order.

First of all, when both of the first and second path selection valves 41 and 42 are closed and both of the first and second bypass valves 52 are opened, the third measuring path is formed. The third measuring path is formed as a path along which raw water passes through the raw water supply part 200, the first bypass line 71, the first filtration membrane 110, the second path line 22, the second bypass line 72, the second filtration membrane 120, the third path line 23, and the third filtration membrane 130 and flows to the first flow rate measuring part 310.

In this way, the raw water from the raw water supply part 200 sequentially passes through the first filtration membrane 110, the second filtration membrane 120, and the third filtration membrane 130 and flows to the first flow rate measuring part 310, and the pollution index measuring part 400 measures the pollution index of the third filtration membrane 130 on the basis of the flow rate of water introduced into the first flow rate measuring part 310.

Figure 3:
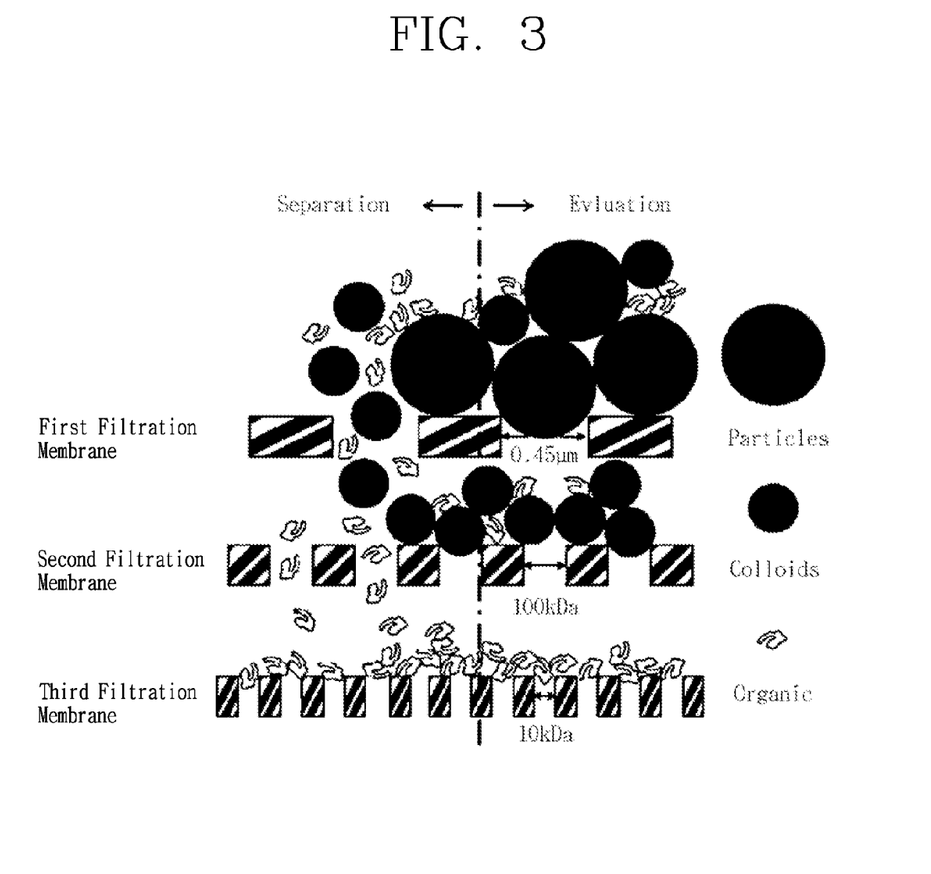
FIG. 3 is a view for explaining the permeation characteristics of first, second, and third filtration membranes in the device for measuring the pollution index of a filtration membrane according to the second embodiment of the present invention.

FIG. 3 is a view conceptually illustrating foreign substances passed through the first, second, and third filtration membranes 110, 120, and 130 and foreign substances subject to evaluation in the device for measuring the pollution index of a filtration membrane according to the second embodiment of the present invention. FIG. 3 is illustrated by taking an example where the first filtration membrane 110 is a hydrophilic microfiltration membrane MF having a pore size of 0.45 µm, the second filtration membrane 120 is a hydrophilic ultrafiltration membrane UF having a molecular weight cut off of 100 kDa, and the third filtration membrane 130 is a hydrophilic nanofiltration membrane NF having a molecular weight cut off of 10 kDa.

FIG. 3 conceptually illustrates that, among the foreign substances contained in raw water, common suspended particles are filtered through the first filtration membrane 110, colloidal are filtered through the second filtration membrane 120, and organic matters are filtered through the third filtration membrane 130.

As shown in FIG. 3, since common suspended particles and colloids are filtered through the first filtration membrane 110 and the second filtration membrane 120, only organic matters required to evaluate the pollution index of the third filtration membrane 130 can be used for the measurement of the pollution index of the third filtration membrane 130.

As described above, once the measurement of the pollution index of the third filtration membrane 130 is completed, the second path selection valve 42 is opened and the second bypass valve 52 is closed while the first path selection valve 41 is kept closed and the first bypass valve 51 is kept opened, thereby forming the second measuring path.

The second measuring path is formed as a path along which raw water passes through the raw water supply part 200, the raw water supply line 10, the first bypass line 71, the first filtration membrane 110, the second path line 22, and the second filtration membrane 120 and flows to the first flow rate measuring part 310.

In this way, the raw water from the raw water supply part 2000 sequentially passes through the first filtration membrane 110 and the second filtration membrane 120 and flows to the first flow rate measuring part 310, and the pollution index measuring part 400 measures the pollution index of the second filtration membrane 120 on the basis of the flow rate of water introduced into the first flow rate measuring part 310. Referring to FIG. 3, while suspended particles have been filtered through the first filtration membrane 110, colloids are deposited or adsorbed on the second filtration membrane 120 and foul the second filtration membrane 120. On the other hand, organic matters, which are small in size, are passed through the second filtration membrane 120, having no effect on fouling of the second filtration membrane 120.

When the measurement of the pollution index of the second filtration membrane 120 is completed through the second measuring path, the second bypass valve 52 is closed and the first path selection valve 41 is opened to form the first measuring path. The first measuring path is formed as a path along which raw water passes through the raw water supply part 200, the raw water supply line 10, the first filtration membrane 110, and the first path line 21 and flows to the first flow rate measuring part 310.

As described above, only the suspended solids affecting the pollution indexes of the first, second, and third filtration membranes 110, 120, and 130 are filtered through the first, second, and third filtration membranes 110, 120, and 130, thereby enabling more accurate prediction of membrane fouling.

Although the foregoing embodiment has been described with respect to an example where the pollution indexes of the first, second, and third filtration membranes 110, 120, and 130 are measured in descending order, they may be measured in ascending order. The on and off states of the first and second path selection valves 41 and 42 and the first and second bypass valves 51 and 52 for forming the first, second, and third measuring paths for measuring the first, second, and third filtration membranes 110, 120, and 130, respectively, are as described above.

The device for measuring the pollution index of a filtration membrane according to the second embodiment of the present invention may include a first path control valve 81, a second path control valve 82, and a third path control valve 83. The first path control valve 81 is installed on the inlet side of the first pressure regulator 61 of the raw water supply line 10 so as to be connected in parallel to the first bypass valve 51. The second path control valve 82 is installed on the inlet side of the second pressure regulator 62 of the second path line 22 so as to be connected in parallel to the second bypass valve 52. The third path control valve 82 is installed on the inlet side of the third pressure regulator 63 of the third path line 23.

The first path control valve 81 is opened or closed in reverse to the way the first bypass valve 51 is opened or closed. That is, when forming the first measuring path, the first bypass valve 51 is closed and the first path control valve 81 is opened and raw water flows into the first filtration membrane 110 through the first pressure regulator 61. On the other hand, when forming the second measuring path and the third measuring path, the first bypass valve 51 is opened and the first bypass control valve 81 is closed and raw water flows into the first filtration membrane 110 through the first bypass line 71.

The second path control valve 82 is closed when forming the first measuring path and the third measuring path, and it is opened when forming the second measuring path. Accordingly, once the first measuring path is formed, raw water is prevented from flowing to the second pressure regulator 62, thereby allowing the raw water to pass through the first filtration membrane 110 and then immediately flowing to the first flow rate measuring part 310.

Moreover, the second path control valve 82 is closed when the second measuring path is opened, thereby allowing raw water to pass through the second filtration membrane 120 by means of the second pressure regulator 62. Also, the second path regulation valve 82 is closed when forming the third measuring path, thereby allowing raw water to pass through the second filtration membrane 120 via the second bypass line 72.

In addition, the third path control valve 83 is closed when forming the first measuring path and the second measuring path, and opened when forming the third measuring path.

Therefore, like the foregoing first embodiment, the first, second, and third measuring paths can be formed in a more stable manner than preventing the flow of raw water only by means of the first and second pressure regulators 61 and 62.

Third Embodiment

Hereinafter, the configuration of a device for measuring the pollution index of a filtration membrane according to a third embodiment of the present invention will be described in detail with reference to FIG. 4. The device for measuring the pollution index of a filtration membrane according to the third embodiment of the present invention uses three filtration membranes having different pore characteristics, and includes more components in addition to those in the first embodiment. The components corresponding to those of the first embodiment are denoted by the same reference numerals, and a description thereof can be omitted.

The third embodiment of the present invention will be described on an example where the hydrophilic microfiltration membrane MF is used as the first filtration membrane 110, the hydrophilic ultrafiltration membrane is used as the second filtration membrane 120, and the hydrophilic nanofiltration membrane NF is used as a third filtration membrane 130.

Figure 4:
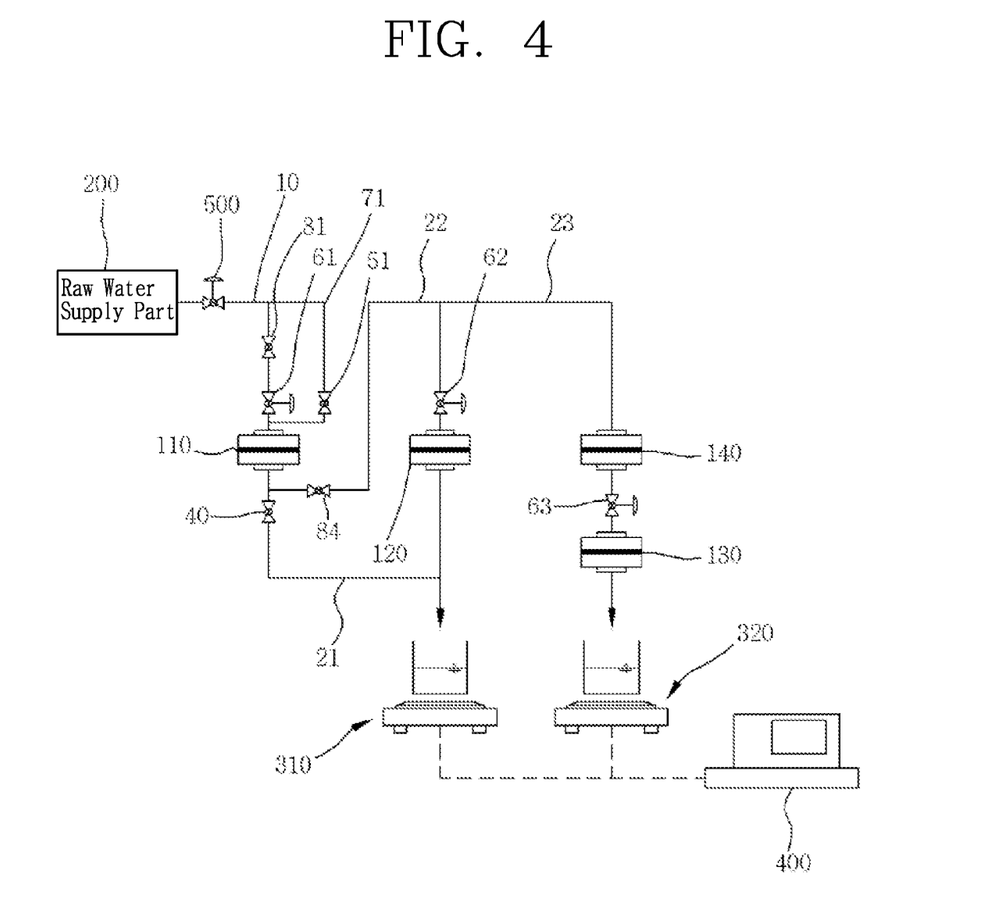
FIG. 4 is a view showing the configuration of a device for measuring the pollution index of a filtration membrane according to a third embodiment of the present invention.

Referring to FIG. 4, the device for measuring the pollution index of a filtration membrane according to the third embodiment of the present invention includes a raw water supply part 200, a raw water supply line 10, a first filtration membrane 110, a second filtration membrane 120, a third filtration membrane 130, a first flow rate measuring part 310, a first path line 21, a second path line 22, a third path line 23, a first path selection valve 41, an auxiliary filtration membrane 140, a first flow rate measuring part 310, a second flow rate measuring part 320, and a pollution index measuring part 400. The basic configurations of the raw water supply part 200, the raw water supply line, and the first flow rate measuring part 310 are identical to those of the first embodiment, so a detailed description thereof will be omitted.

The first path line 21 connects the first filtration membrane 110 to the first flow rate measuring part 310 so that the raw water filtered through the first filtration membrane 110 flows to the first flow rate measuring part 310. The second path line 22 is connected in parallel to the first path line 21, like the first embodiment.

The first path selection valve 41 is installed on the first path line 31 so as to be connected in parallel to the second filtration membrane 120. The first path selection valve 41 is opened to form a first measuring path and closed to form second and third measuring paths, and a detailed description of which will be made later.

The third path line 23 is branched from the inlet side of the second filtration membrane 120 of the second path line 22. The auxiliary filtration membrane 140 and the third filtration membrane 130 are sequentially installed on the third path line 23. That is, the third filtration membrane 130 is installed on the third path line 23, and the auxiliary filtration membrane 140 is installed on the inlet side of the third filtration membrane 130 of the third path line 23.

The pores of the auxiliary filtration membrane 140 are equal in size to those of the second filtration membrane 120. For example, if the second filtration membrane 120 is a hydrophilic ultrafiltration membrane UF, the auxiliary filtration membrane 140 also may be a hydrophilic ultrafiltration membrane UF. The second flow rate measuring part 320 is installed on the outlet side of the third filtration membrane 130 of the third path line 23 to measure the flow rate of raw water filtered through the third filtration membrane 130.

As shown in FIG. 4, the device for measuring the pollution index of a filtration membrane according to the third embodiment of the present invention may include a first pressure regulator 61, a first bypass line 71, and a first bypass valve 51. Moreover, the device for measuring the pollution index of a filtration membrane may include a second pressure regulator 62, a second bypass line 72, a second bypass valve 52, and a third pressure regulator 63.

The first pressure regulator 61 is installed on the inlet side of the first filtration membrane 110 of the raw water supply line 10 to regulate the pressure of raw water introduced into the first filtration membrane 110. The first bypass line 71 is connected in parallel to the raw water supply line 10 to bypass the first pressure regulator 61.

The first bypass valve 51 is installed on the first bypass line 71. When the first measuring path is formed, i.e., the first path selection valve 41 is opened, the first bypass valve 51 is closed to let the raw water supplied through the raw water supply line 10 into the first filtration membrane 110 through the first pressure regulator 61.

On the other hand, when the second measuring path and the third measuring path are formed, i.e., the first path selection valve 41 is closed, the first bypass valve 51 is opened to let the raw water supplied through the raw water supply line 10 into the first filtration membrane 110 through the first bypass line 71.

According to the above configuration, a process for the pollution index measuring part 400 to measure the pollution index of the first filtration membrane 110 by forming the first measuring path and simultaneously measure the pollution indexes of the second and third filtration membranes 130 by simultaneously forming the second and third measuring paths will be described in detail.

First of all, when the first bypass valve 51 is closed and the first path selection valve 41 is opened, the first measuring path is formed. The first measuring path is formed as a path along which raw water passes through the raw water supply part 200, a first filter, and the second path line 22 and flows to the first flow rate measuring part 310. The pollution index measuring part 400 measures the pollution index of the first filtration membrane 110 on the basis of the flow rate measured by the first flow rate measuring part 310.

Once the measurement of the pollution index of the first filtration membrane 110 is completed, the first bypass valve 51 and the first path selection valve 41 are opened to simultaneously form the second and third measuring paths. The second measuring path is formed as a path along which raw water passes through the raw water supply part 200, the raw water supply line 10, the first bypass line 71, the first filtration membrane 110, the second path line 22, and the second filtration membrane 120 and flows to the first flow rate measuring part 310. The third measuring path is formed as a path along which raw water passes through the raw water supply part 200, the raw water supply line 10, the first bypass line 71, the first filtration membrane 110, the second path line 22, the third path line 23, the auxiliary filtration membrane 140, and the third filtration membrane 130 and flows to the second flow rate measuring part 320.

As described above, the second and third path lines 22 and 23 are simultaneously formed, the flow rate of raw water filtered through the second filtration membrane 120 and the flow rate of raw water filtered through the third filtration membrane 130 are measured by the first and second flow rate measuring parts 310 and 320, respectively. Thus, the pollution indexes of the second and third filtration membranes 120 and 130 can be simultaneously measured.

The device for measuring the pollution index of a filtration membrane according to the third embodiment of the present invention may include a first path control valve 81 and a fourth path control valve 84. The first path control valve 81 is installed on the inlet side of the first pressure regulator 61 of the raw water supply line 10 so as to be connected in parallel to the first bypass valve 51. The fourth path control valve 84 is installed on the second path line 22.

The first path control valve 81 is opened or closed in reverse to the way the first bypass valve 51 is opened or closed. That is, when forming the first measuring path, the first bypass valve 51 is closed and the first path control valve 81 is opened and raw water flows into the first filtration membrane 110 through the first pressure regulator 61. On the other hand, when forming the second measuring path, the first bypass valve 51 is opened and the first bypass control valve 81 is closed and raw water flows into the first filtration membrane 110 through the first bypass line 71.

The fourth path control valve 84 is installed on the second path line to control the inflow of raw water into the second path line 22, and closed when forming the first measuring path and opened when forming the second measuring path.

Accordingly, once the first measuring path is formed, raw water is completely prevented from flowing to the second path line 22, and once the second measuring path is formed, raw water is likewise prevented from flowing to the first pressure regulator 61. Therefore, the first and second measuring paths can be formed in a more stable manner than preventing the flow of raw water only by means of the first, second, and third pressure regulators 61, 62, and 63.

The foregoing embodiments have been described with respect to an example where the second and third embodiments provide an extended structure in addition to the basic structure of the first embodiment. The technical spirit of the present invention is not limited to the second and third embodiments in which three filtration membranes 110, 120, and 130 are used, and it will be apparent to those skilled in the art that four or more filtration membranes can be used according to the second and third embodiments.

Fourth Embodiment

Hereinafter, the configuration of a device for measuring the pollution index of a filtration membrane according to a fourth embodiment of the present invention will be described in detail with reference to FIG. 5. The device for measuring the pollution index of a filtration membrane according to the fourth embodiment of the present invention includes a raw water supply part 200, a raw water supply line 10, a plurality of filtration membranes 110, 120, and 130, path lines 21a, 22a, and 23a, and a plurality of flow rate measuring parts 310a, 310b, and 310c, at least one auxiliary filtration membrane 140a and 140b, and a pollution index measuring part 400.

The raw water supply part 200 supplies raw water to be measured. The raw water supply part 200 is configured to supply raw water in a pressurized condition, and uses compressed air, a pump, etc. For a seawater desalination plant, raw water may be supplied in a compressed state by a high-pressure pump of the plant.

The plurality of filtration membranes 110, 120, and 130 have different filtration properties. In an example of the present invention, the plurality of filtration membranes 110, 120, and 130 have different pore sizes and the number of these filtration membranes 110, 120, and 130 is three. The pore sizes of the first, second, and third filtration membrane 110, 120, and 130 are ranked in ascending order. A description will be made on an example where the first filtration membrane 110 is a hydrophilic microfiltration membrane, the second filtration membrane 120 is a hydrophilic ultrafiltration membrane 120, and the third filtration membrane 130 is a hydrophilic nanofiltration membrane NF.

Figure 5:
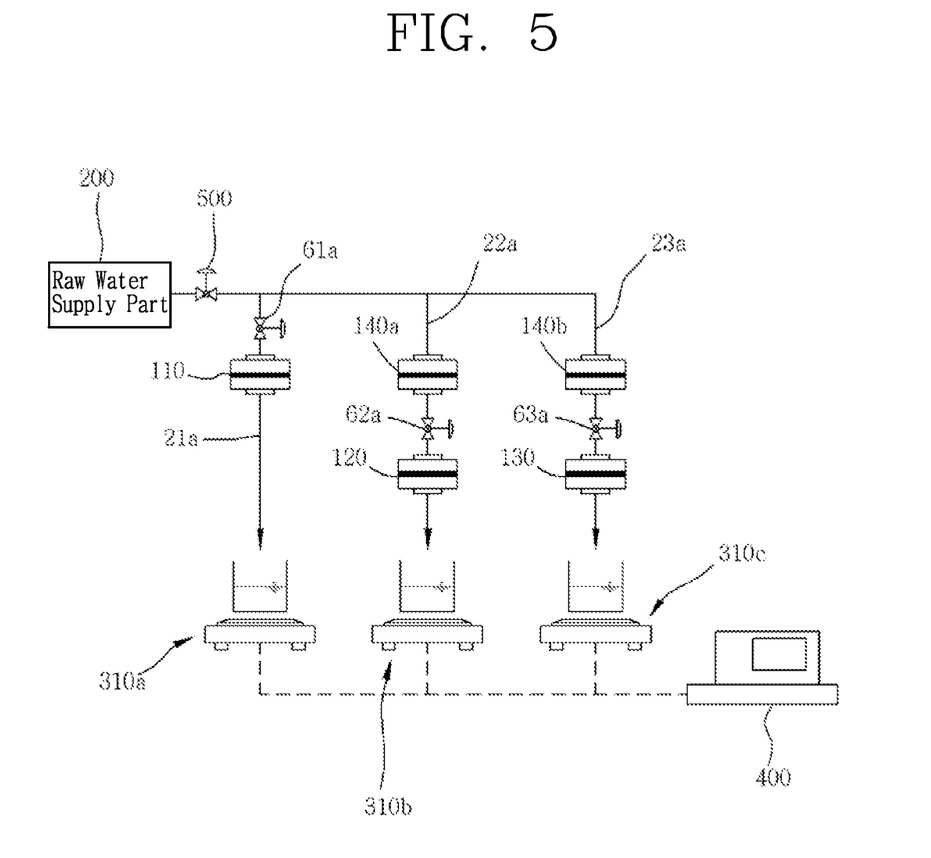
FIG. 5 is a view showing the configuration of a device for measuring the pollution index of a filtration membrane according to a fourth embodiment of the present invention.

As shown in FIG. 5, the path lines 21a, 22a, and 23a connect the first, second, and third filtration membranes 130 in parallel to the raw water supply part 200. As used herein, the path line 21a with the first filtration membrane 110 installed thereon is referred to as the first path line 21a, the path line 22a with the second filtration membrane 120 installed thereon is referred to as the second path line 22a, and the path line 23a with the third filtration membrane 130 installed the auxiliary hereon is referred to as the third path line 23a.

The auxiliary filtration membranes 140a and 140b, the second filtration membrane 120, and the third filtration membrane 130 are installed on their respective inlet sides. More specifically, the first auxiliary filtration membrane 140a is installed on the inlet side of the second filtration membrane 120 of the second path line 22a, and the second auxiliary filtration membrane 140b is installed on the inlet side of the third filtration membrane 130 of the third path line 23a.

The first auxiliary filtration membrane 140a and the second filtration membrane 120 have different filtration properties. The pores of the first auxiliary filtration membrane 140a are larger than the pores of the second filtration membrane 120. For example, the pores of the first auxiliary filtration membrane 140a are equal in size to those of the first filtration membrane 110, and the raw water introduced into the second filtration membrane 120 is brought into the same condition as the water passed through the first filtration membrane 110.

Likewise, the second auxiliary filtration membrane 140b and the third filtration membrane 130 have different filtration properties. The pores of the second auxiliary filtration membrane 140b are larger than the pores of the third filtration membrane 130. the pores of the second auxiliary filtration membrane 140b are equal in size to those of the second filtration membrane 120, and the raw water introduced into the third filtration membrane 130 is brought into the same condition as the water passed through the second filtration membrane 120.

Pressure regulators 61a, 62a, and 63a for regulating the pressure of raw water introduced into the first, second, and third filtration membranes 110, 120, and 130 may be installed on the inlet sides of the first, second, and third filtration membranes 110, 120, and 130.

The first flow measuring part 310a is installed on the outlet side of the first filtration membrane 110 to measure the flow rate of raw water passed through the first filtration membrane 110, the second flow rate measuring part 310b is installed on the outlet side of the second filtration membrane 120 to measure the flow rate of raw water passed through the second filtration membrane 120, and the third flow rate measuring part 310c is installed on the outlet side of the third filtration membrane 130 to measure the flow rate of raw water passed through the third filtration membrane 130.

According to the above configuration, the raw water supplied from the raw water supply part 200 passes through the first, second, and third filtration membranes 110, 120, and 130 connected in parallel by the path lines 21a, 22a, and 23a and then introduced into the first, second, and third measuring parts 310a, 310b, and 310c, and the pollution index measuring part 400 measures the pollution indexes of the first, second, and third filtration membranes 110, 120, and 130 on the basis of the flow rates measured by the first, second, and third flow rate measuring parts 310a, 310b, and 310c.

As described above, the embodiments of the present invention will be described with appropriately referring to drawings. However, the present invention should not be construed by limiting to these embodiments, and various changes, modifications, and improvements may be made on the basis of knowledge of a person of ordinary skill as long as they do not deviate from the range of the present invention.

The invention claimed is:

1. A device for measuring the pollution index of a filtration membrane, the device comprising:
    a raw water supply part supplying raw water to be measured;
    a first filtration membrane;
    a raw water supply line connecting the raw water supply part to the first filtration membrane;
    a first flow rate measuring part measuring the flow rate;
    a first path line connecting the first filtration membrane to the first flow rate measuring part;
    a second path line connected to the first path line in parallel;
    a second filtration membrane installed in the second path line and having a filtration characteristic different from the first filtration membrane;
    a first path selection valve installed in the first path line in parallel with respect to the second filtration membrane so that a first measuring path through which the raw water flows from the raw water supply part to the first flow rate measuring part passes through the first filtration membrane without flowing through the second filtration membrane and a second measuring path through which the raw water flows from the raw water supply part to the first flow rate measuring part successively passes through the first filtration membrane and then the second filtration membrane; and
    a pollution index measuring part measuring the pollution indexes of the first filtration membrane and the second filtration membrane on the basis of the flow rate measured by the first flow rate measuring part with respect to the first measuring path and the second measuring path.

2. The device of claim 1, wherein the pores of the first filtration membrane are larger than the pores of the second filtration membrane.

3. The device of claim 2, the device comprising:
    a first pressure regulator installed on the inlet side of the first filtration membrane of the raw water supply line to regulate the pressure of raw water introduced into the first filtration membrane;
    a first bypass line connected to the raw water supply line to bypass the first pressure regulator; and
    a first bypass valve installed on the first bypass line, and closed to form the first measuring path and opened to form the second measuring path and the third measuring path.

4. The device of claim 3, further comprising a second pressure regulator installed on the inlet side of the second filtration membrane of the second path line to regulate the pressure of raw water introduced into the second filtration membrane.

5. The device of claim 3, wherein the second path line comprises a second inlet path line forming the inlet side of the second filtration membrane and a second outlet path line forming the outlet side of the second filtration membrane, the device further comprises a third path line connected in parallel to the second outlet path line, a third filtration membrane installed on the third path line and having pores smaller than the pores of the second filtration membrane, and a second path selection valve installed on the second path line in parallel to the third filtration membrane to form a third measuring path, while the first path selection valve is in closed position, along which the raw water from the raw water supply part sequentially passes through the first, second, and third filtration membranes and flows to the first flow measuring part, and the pollution index measuring part measures the pollution index of the third filtration membrane on the basis of the flow rate measured by the first flow rate measuring part with respect to the third measuring path.

6. The device of claim 5, further comprising:
    a second pressure regulator installed on the second inlet path line to regulate the pressure of raw water introduced into the second filtration membrane;
    a second bypass line connected to the second inlet path line to bypass the second pressure regulator; and a second bypass valve installed on the second bypass line, and closed to form the first measuring path and the second measuring path and opened to form the third measuring path.

7. The device of claim 6, further comprising a third pressure regulator installed on the inlet side of the third filtration membrane of the third path line to regulate the pressure of raw water introduced into the third filtration membrane.

8. The device of claim 7, further comprising:
a first path control valve installed on the inlet side of the first pressure regulator of the raw water supply line so as to be connected in parallel to the first bypass valve, and opened or closed in reverse to the way the first bypass valve is opened or closed;
a second path control valve installed on the inlet side of the second pressure regulator of the second path line so as to be connected in parallel to the second bypass valve, and closed to form the first measuring path and the third measuring path and opened to form the second measuring path; and
a third path control valve installed on the inlet side of the third pressure regulator of the third path line and opened to form the third measuring path.

9. The device of claim 5, wherein the pollution index measuring part measures the pollution indexes of the first, second, and third filtration membranes with respect to the first, second, and third filtration membranes, respectively, in descending order.

10. The device of claim 5, wherein the pollution index measuring part measures the pollution indexes of the first, second, and third filtration membranes with respect to the first, second, and third filtration membranes, respectively, in ascending order.

11. The device of claim 2, further comprising:
a third path line branched from the inlet side of the second filtration membrane of the second path line;
a third filtration membrane installed on the third path line and having pres smaller than the pores of the second filtration membrane;
an auxiliary filtration membrane installed on the inlet side of the third filtration membrane of the third path line and having pores equal in size to the pores of the second filtration membrane; and
a second flow rate measuring part installed on the outlet side of the third filtration membrane of the third path line to form a third measuring path along which the raw water from the raw water supply part sequentially passes through the first, auxiliary, and third filtration membranes and flows to the second flow measuring part,
the second measuring path and the third measuring path are formed simultaneously, and
the pollution index measuring part measures the pollution index of the third filtration membrane on the basis of the flow rate measured by the second flow rate measuring part with respect to the third measuring path.

12. The device of claim 11, further comprising:
a first pressure regulator installed on the raw water supply line to regulate the pressure of raw water introduced into the first filtration membrane;
a second pressure regulator installed on the inlet side of the second filtration membrane of the second path line to regulate the pressure of raw water introduced into the second filtration membrane; and
a third pressure regulator installed between the auxiliary filtration membrane of the third path line and the third filtration membrane to regulate the pressure of raw water introduced into the third filtration membrane.

13. The device of claim 12, further comprising:
a first bypass line connected to the raw water supply line to bypass the first pressure regulator; and
a first bypass valve installed on the first bypass line, and closed to form the first measuring path and opened to form the second measuring path and the third measuring path.

14. The device of claim 13, further comprising:
a first path control valve installed on the inlet side of the first pressure regulator of the raw water supply line so as to be connected in parallel to the first bypass valve, and opened or closed in reverse to the way the first bypass valve is opened or closed; and
a fourth path control valve installed on the second path line to control the inflow of raw water to the second path line, and closed to form the first measuring path and opened to form the second measuring path.

15. A device for measuring the pollution index of a filtration membrane, the device comprising:
a raw water supply part supplying raw water to be measured;
a plurality of filtration membranes having different filtration properties;
a path line connecting the plurality of filtration membranes in parallel to the raw water supply part;
a plurality of flow measuring parts installed on the outlet sides of the filtration membranes to correspond to the respective filtration membranes, and measuring the flow rate of raw water passed through the filtration membranes;
at least one auxiliary filtration membrane installed on the inlet side of at least one of the plurality of filtration membranes, and having a different filtration characteristic from that of the at least one filtration membrane; and
a pollution index measuring part measuring the pollution indexes of the filtration membranes on the basis of the flow rates measured by the flow rate measuring parts.

16. The device of claim 15, wherein the plurality of filtration membranes have different pore sizes, and the pores of the auxiliary filtration membrane are larger than the pores of the filtration membranes.

17. The device of claim 15, further comprising pressure regulators respectively installed on the inlet sides of the filtration membranes to regulate the pressure of raw water introduced into the filtration membranes.

* * * * *